United States Patent [19]

McGuire

[11] Patent Number: 5,257,996
[45] Date of Patent: Nov. 2, 1993

[54] SURGICAL PIN PASSER

[76] Inventor: David A. McGuire, 3418 Lakeside Dr., Anchorage, Ak. 99515

[21] Appl. No.: 806,906

[22] Filed: Dec. 13, 1991

[51] Int. Cl.$^5$ .............................................. A61F 2/32
[52] U.S. Cl. .................................................... 606/104
[58] Field of Search ................. 606/104, 97, 103, 72, 606/62, 60, 67, 68

[56] References Cited

U.S. PATENT DOCUMENTS

| | | | |
|---|---|---|---|
| 2,697,433 | 12/1954 | Zehnder | 606/103 |
| 3,351,054 | 11/1967 | Florek | 606/104 |
| 3,892,232 | 7/1975 | Neufeld | 606/104 |
| 4,140,111 | 2/1979 | Morrill | 606/104 |
| 4,381,770 | 5/1983 | Neufeld | 606/67 |
| 4,441,563 | 4/1984 | Walton | 606/104 |
| 4,456,010 | 6/1984 | Reimels | 606/80 |
| 4,549,538 | 10/1985 | Schadrack | 606/104 |
| 4,911,154 | 3/1990 | Vickers | 606/104 |
| 4,920,958 | 5/1990 | Walt | 606/103 |
| 4,969,895 | 11/1990 | McLeod | 606/104 |

FOREIGN PATENT DOCUMENTS 0645252 7/1962 Canada .................................. 606/104

Primary Examiner—Michael A. Brown
Attorney, Agent, or Firm—Bromberg & Sunstein

[57] ABSTRACT

A system for the insertion of an object into biological tissue, has in one embodiment a pin and a pin passer, wherein the pin passer has an elongate body and first and second ends, and includes a receiving means for removably receiving the pin and an attachment means for removable attachment of the object. In one embodiment, the attachment means on the pin passer may be located at the second end and the receiving means may be include a notch that has a blind channel for insertion of the pin. The passer may further include a slot, for receiving the pin, extending from the notch proximal to the second. The slot is suitably configured to engage the pin securely, so that the pin may be removably inserted into the blind channel in the slot and secured into place in the slot. In an embodiment of the method according to the invention, the system of the invention may be utilized, in anterior cruciate ligament reconstruction surgery, to insert a bone-tendon-bone autograft into the knee.

22 Claims, 16 Drawing Sheets

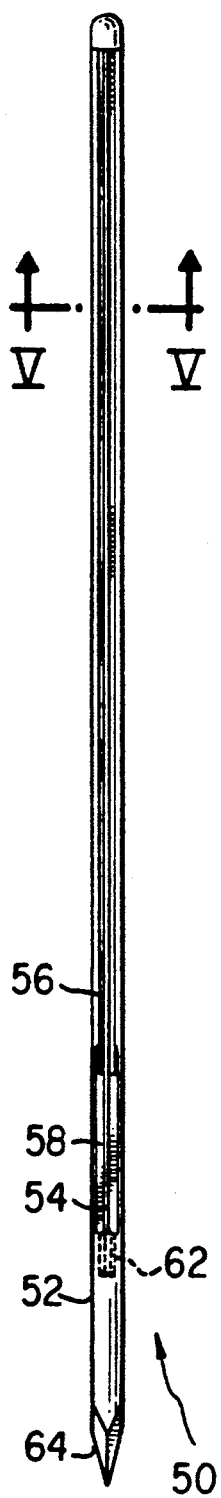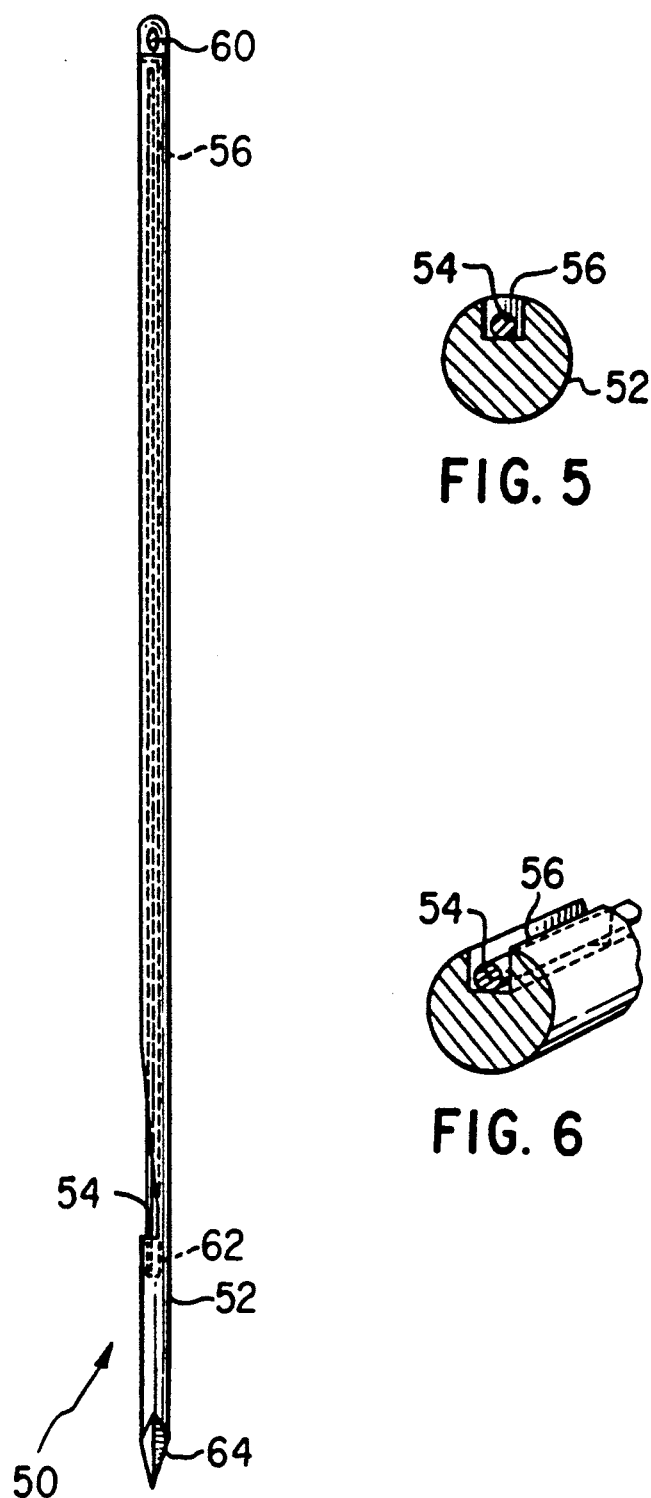
FIG. 3
FIG. 4
FIG. 5
FIG. 6

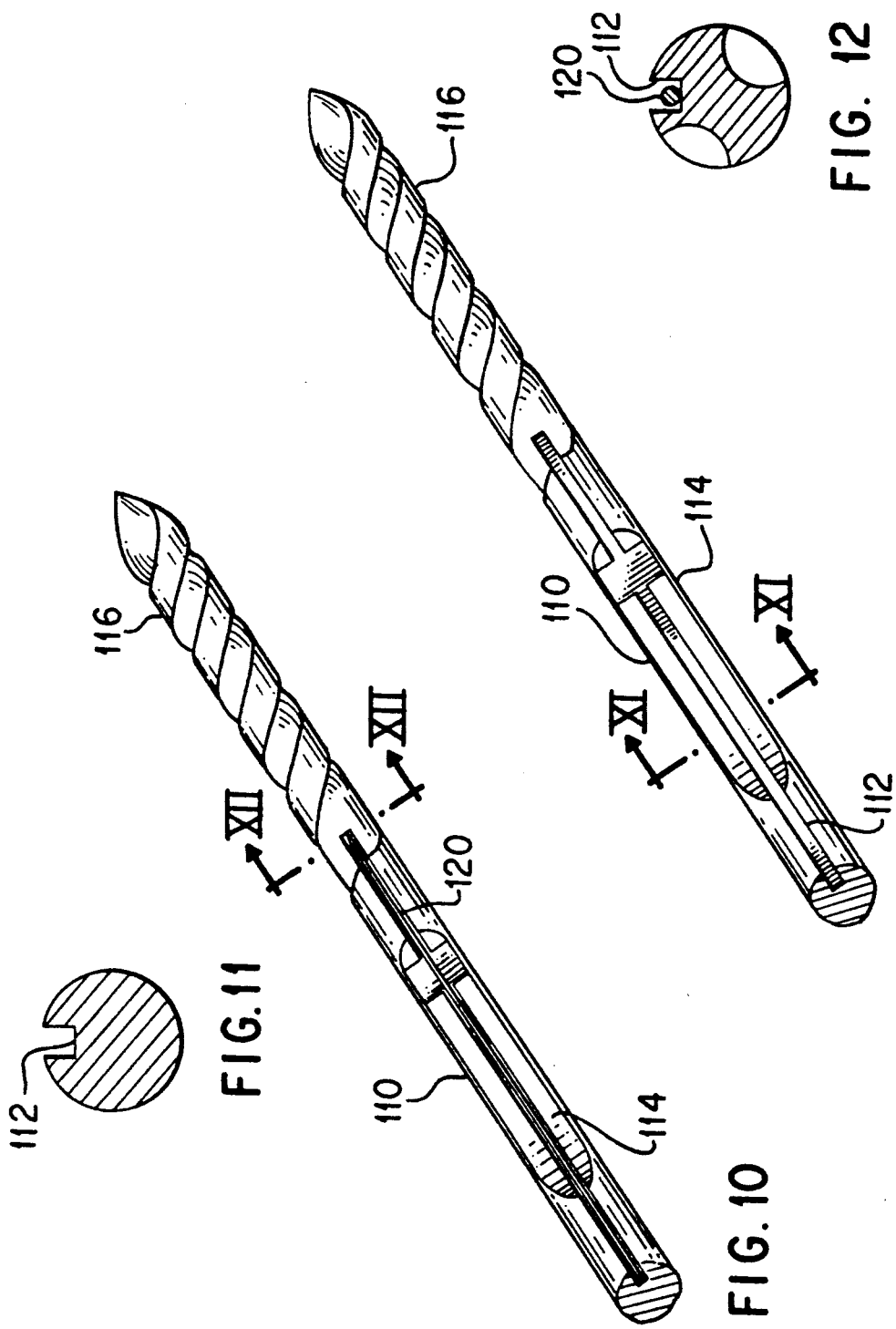

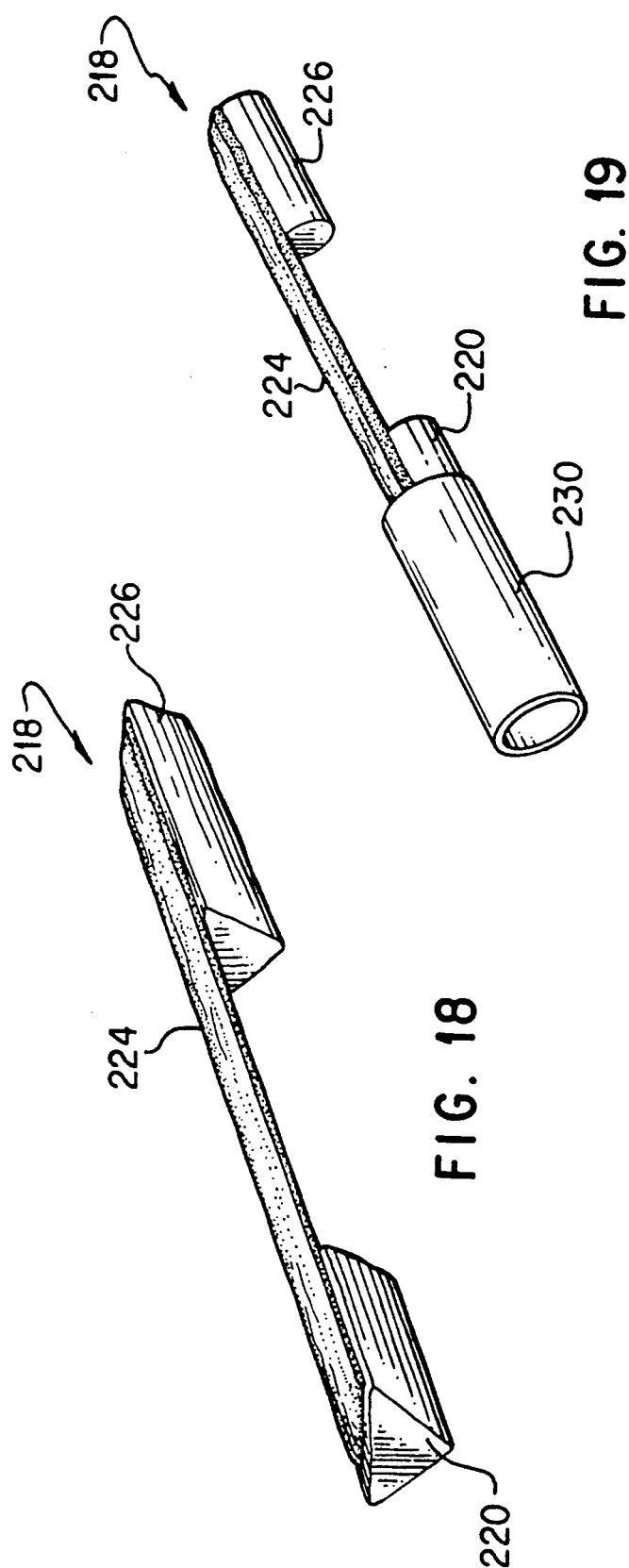

SURGICAL PIN PASSER

TECHNICAL FIELD

This invention relates to devices and methods for the insertion of objects in a tissue.

BACKGROUND ART

In the prior art, various techniques have been utilized for the insertion of objects into biological tissue. Asnis et al. discloses a surgical guide pin system, including a guide pin located in a longitudinal bore within a cylindrical external sleeve, wherein the guide pin is longer than the cylindrical sleeve, and wherein the system is inserted into the proximal side of the bone, but does not pass through and out of the distal side of the bone and then the external sleeve is removed, leaving the guide pin in. Asnis et al. (1983) U.S. Pat. Nos. 4,383,527 and (1984) 4,450,835. Purnell discloses an apparatus for cruciate ligament reconstruction which utilizes femoral and tibial targeting hooks to insert a ligament graft into the tibia and femur. Purnell et al. (1988) U.S. Pat. No. 4,781,182. Watanabe discloses a guide for anterior cruciate ligament reconstruction that includes a wire with a cone slidably mounted on one end of the wire, wherein the wire contains a loop at one end and a ball at the other end. The wire may be inserted into the femur and is then grabbed by a wire grasper in the tibia and pulled through the tibia. A tendon is then tied to the end of the loop and the tendon is pulled through the hole in the tibia and the femur. Watanabe (1990) U.S. Pat. No. 4,946,462. Rosenoff teaches a drill pin which is used to drill a hole through the tibia and femur, and then a ligament prosthesis is threaded through an eye on the end of the pin and the pin and ligament are pulled through and the prosthesis is sutured. Rosenoff et al. (1966) J. Am. Vet. Med. Assoc. 149 pp. 523-524.

SUMMARY OF THE INVENTION

The present invention provides in one embodiment a system for the insertion of an object into biological tissue, which includes a pin and a pin passer, wherein the pin passer has an elongate body and first and second ends, and includes a receiving means for removably receiving the pin and an attachment means for removable attachment of the object. In one embodiment, the attachment means on the pin passer may be located at the second end and the receiving means may include a notch that has a blind channel for insertion of the pin. The passer may further include a slot, for receiving the pin, extending from the notch proximal to the second end. The slot is suitably configured to engage the pin securely, so that the pin may be removably inserted into the blind channel in the slot and secured into place in the slot. In an embodiment of the method according to the invention, the system of the invention may be utilized, in anterior cruciate ligament reconstruction surgery, to insert a bone-tendon-bone autograft into the knee.

BRIEF DESCRIPTION OF FIGURES

The foregoing features of the invention will be more readily understood by consideration of the following detailed description, taken with the accompanying drawings, in which:

FIG. 3 depicts one embodiment of the pin passer of the invention.

FIG. 4 is a side view of the pin passer shown in FIG. 3.

FIG. 5 is a cross section, across the line V—V, of the pin passer shown in FIG. 3.

FIG. 6 is a cutaway section view, across the line V—V, of the pin passer shown in FIG. 3.

FIG. 9 is an expanded view of the fluted first end of the pin passer shown in FIG. 7.

FIG. 10 depicts the pin passer of FIG. 9, with a guide pin in place in the passer.

FIG. 11 depicts a cross section of the passer of FIG. 9 taken along the line XI—XI.

FIG. 12 depicts a cross section of the passer of FIG. 10, taken along the line XII—XII.

FIGS. 15-25 illustrate an embodiment of the method of the invention in practicing anterior cruciate ligament reconstruction, and FIG. 15 depicts the vertical incisions in the knee used in such reconstruction.

FIG. 16 depicts the notchplasty contour utilized in the anterior cruciate ligament reconstruction method.

FIG. 17 depicts the patellar tendon bone autograft utilized in the anterior cruciate ligament reconstruction method.

FIG. 18 depicts the bone-tendon-bone autograft utilized in the anterior cruciate ligament reconstruction method.

FIG. 19 depicts the bone-tendon-bone autograft and sizing tube utilized in the anterior cruciate ligament reconstruction method.

FIG. 20 depicts a drill guide used for drilling a drill hole in the bone-tendon-bone graft.

FIG. 21 depicts a tibial drill guide, which is used for drilling the bone tunnels in the anterior cruciate ligament reconstruction method.

FIG. 22 depicts a reamer for use in chamfering the edges of the bone tunnels.

FIG. 23 depicts an embodiment of the pin passer system (in accordance with FIG. 3) in place within the knee.

FIG. 24 depicts the insertion of a headless cannulated screw according to the method.

FIG. 25 depicts a bone-tendon-bone autograft in place in the knee in accordance with the method.

DETAILED DESCRIPTION OF SPECIFIC EMBODIMENTS

A. General

The invention provides a system for the insertion of an object into biological tissue, which includes a pin and a pin passer. The pin passer may be comprised of an elongate body, having first and second ends, and including pin receiving means for removably receiving the pin and an object attachment means for removably attaching the object. The attachment means for removably attaching the object may be located at the second end of the passer. The receiving means for removably receiving the passer may include a notch, and the notch may include a blind channel for insertion of the pin. According to the methods of the invention, the system, including the pin passer and pin engaged thereto, may be inserted through the biological tissue. The pin and pin passer may then be disengaged, and an object may be attached to the second end of the passer. The passer may then be pulled through the tissue from its first side, thereby pulling the object, such as a graft, into place in the tissue, while leaving the pin in place. The pin may then be used for guiding the insertion of objects such as screws or sutures into the tissue.

Figure 1:
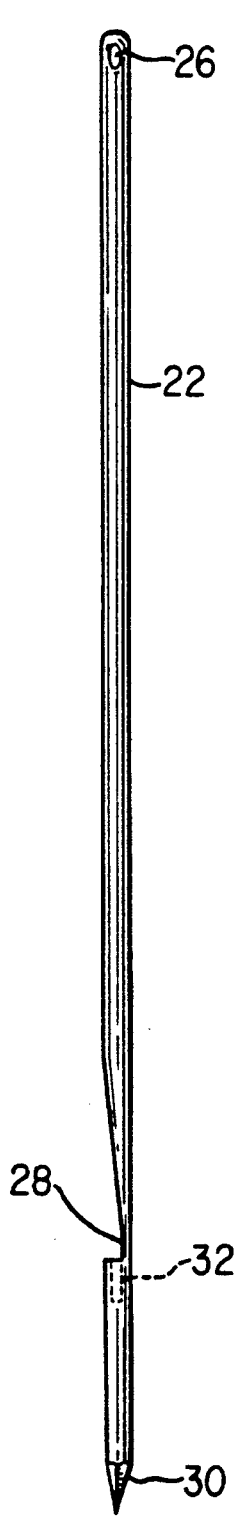
FIG. 1 depicts one embodiment of the pin passer of the invention.
Figure 2:
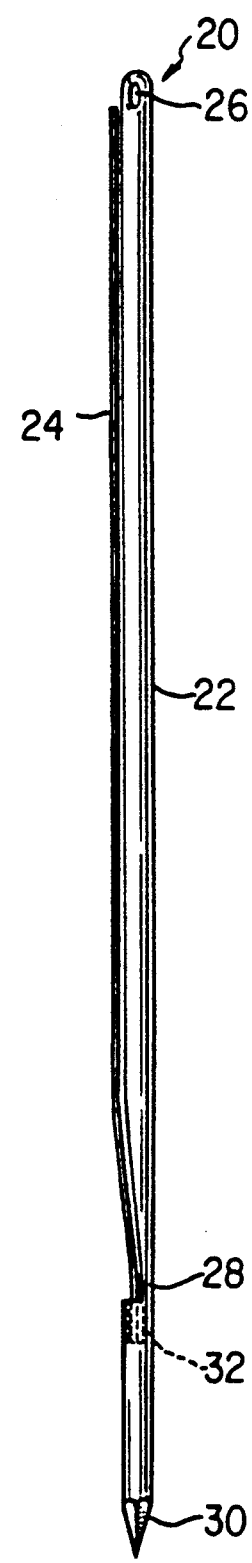
FIG. 2 depicts the pin passer of FIG. 1, with a guide pin in place in the pin passer.

One embodiment of the pin passer system of the invention, including pin passer 22 and pin 24, is shown in FIGS. 1 and 2. The pin passer 22, shown in FIG. 1, has a elongate body with first and second ends, wherein the first end includes point 30. At the second end of the pin passer 22 is an arrangement, implemented by eye 26, for attaching a suture connected in turn to a graft or another suitable object. The pin passer 22 also includes notch 28, which includes blind channel 32, into which the pin 24 may be inserted. FIG. 2 shows the pin passer system 20 with pin 24 in place in the blind channel 32 of pin passer 22. The point allows the passer to be inserted through soft tissue by the application of pressure, and also allows the passer to be driven through hard tissue, such as bone, with a mallet.

The pin passer of the invention may also include a slot extending from the notch to the second end of the passer, wherein the slot is suitably configured to securely engage the pin, such that the pin may be removably inserted into the blind channel in the notch and then secured into place in the slot. One embodiment of the passer system of the invention is illustrated in FIG. 3, which includes the pin passer 52 with pin 54 in place in the passer. The passer 52 includes a notch 58, and includes a point 64 at its first end. The passer 52 also includes slot 56, which extends from the notch to the second end, wherein the slot is suitably configured for secure engagement with the pin. The second end of the passer includes eye 60 for attachment of the object that is to be inserted into the tissue. Located in notch 58 is blind channel 62. Upon insertion of the guide pin 54 into blind channel 62 in notch 58, the guide pin 54 is slid into place in the slot and fits tightly into the slot at both ends. The length of the guide pin may be equal to the combined length of the slot and the blind channel, allowing a tight fit of the pin. The width of the slot may be slightly greater than the width of the pin. The notch allows the pin to be placed in the passer before insertion through the tissue, and then to be removed from the pin after insertion.

A side view of the passer 50 is shown in FIG. 4. FIGS. 5 and 6 show cross sectional and cutaway views respectively, along the line V—V, of the system shown in FIG. 3. FIGS. 5 and 6 illustrate slot 56 with pin 54 in place in the slot.

In one embodiment, the pin passer system of the invention may be utilized to insert objects through previously drilled bone tunnels. The passer system and pin allow screws, sutures or other objects to be placed in the same drill hole for any purpose.

In an embodiment of the method of the invention, the system of the invention may be used in anterior cruciate ligament reconstruction. The pin may be comprised of a flexible steel composite, such as Nitinol ™, approximately 0.064 inches in diameter and approximately 9 to 14 inches in length. The pin may be ground down at the tip so that it fits into a slot on the pin passer, and the slot and blind channel in the notch may be suitably configured for secure engagement with the guide wire. The flexible steel composite of the pin permits bending, but is capable of returning to its original form, which here is designed to be straight. In an alternative embodiment of the invention, the pin passer may be curved. The notch in the pin passer may be disposed at an angle of approximately 3° to 8° with respect to the passer, and may serve as an insertion point for the pin, which produces an arc in the pin when it is inserted. When pressured into the slot, the pin sits flush, and its top coincides with the end view contour of the passer.

Figure 7:
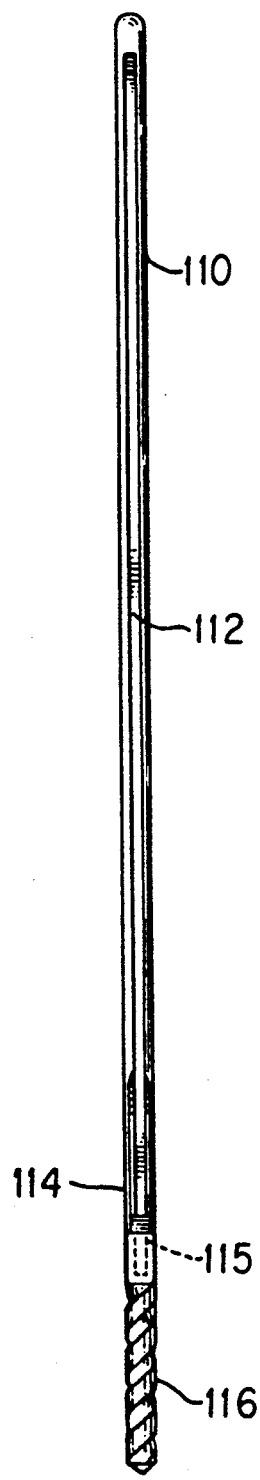
FIG. 7 depicts another embodiment of the pin passer system of the invention.

In another embodiment of the invention, shown in FIG. 7, the first end 116 of the passer 110 may be formed with a twist drill tip or otherwise fluted, to provide a pin passer system that may be removably attached to a drill chuck and inserted into tissue such as bone by drilling. The pin passer 110 includes a slot 112, which extends from a notch 114, to the second end, which contains eye 118. The notch includes blind channel 115, for insertion of a pin, configured for engagement with a mated pin, which fits into the blind channel and the slot. The slot may further also extend, in another embodiment, from the notch to the first end.

Figure 8:
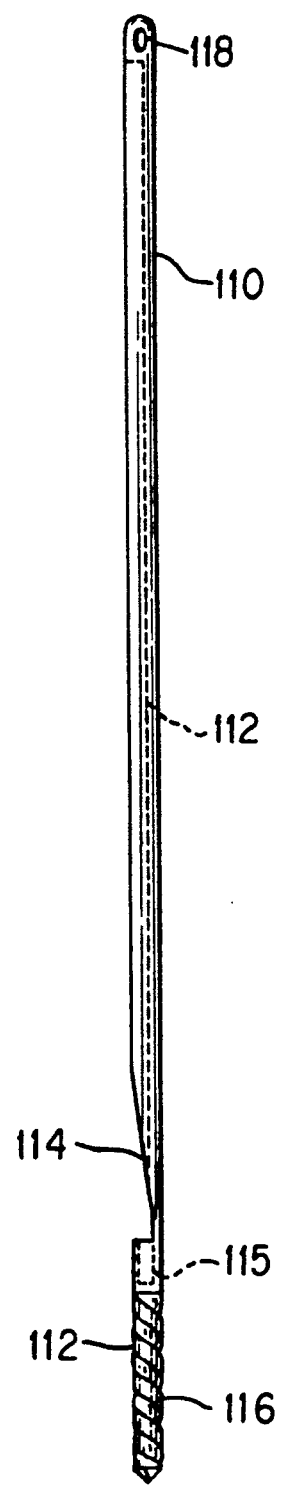
FIG. 8 depicts a side view of the pin passer shown in FIG. 7.

FIG. 8 shows a side view of the passer 110, shown in FIG. 7. FIG. 9 is an expanded view of the fluted first end 116, with twist drill tip, of the pin passer shown in FIGS. 7 and 8. FIG. 10 shows the passer of FIG. 9 with guide pin 120 in place in slot 112. FIG. 11 is a cross section, along the line XI—XI, of passer 110, shown in FIG. 9. FIG. 12 is a cross section of passer 110, along the line XII—XII, shown in FIG. 10, with the guide pin 120 in place in slot 112. The system may be inserted into a drill chuck, tightened, and used as a drill bit. After the drilling procedure is completed, the chuck may be loosened and the drill removed from the system. The system may then be utilized to insert objects into the drilled bone tunnels.

Figure 14:
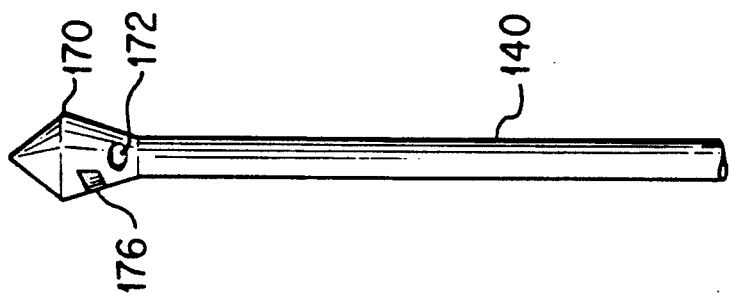
FIGS. 13 and 14 depict a further embodiment of the pin passer system of the invention.
Figure 13:
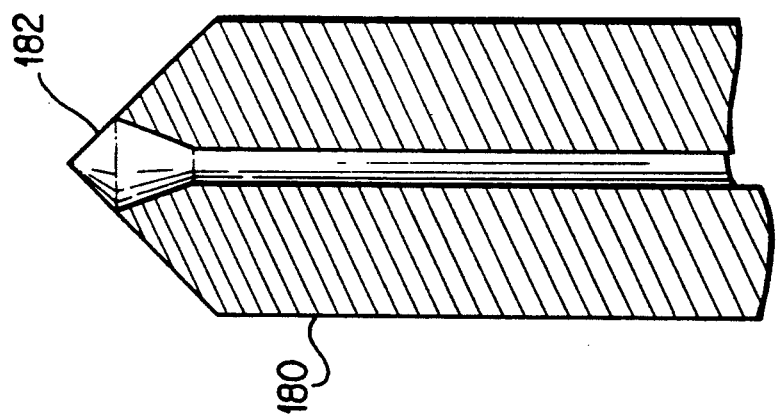

FIGS. 13 and 14 show an alternative embodiment of the system of the invention including passer 180 and pin 140, respectively. The passer 180 includes a channel 182 for removably receiving the pin 140. Pin 140 includes eye 172 and notch 176 for the attachment of an object to be inserted into the tissue. The notch 176 or eye 172 may be configured to permit attachment of a suture or other object in such a fashion as to still permit the complete placement of the pin 140 within the passer channel 182. The pin may be used as a guide for arthroscopic fixation of fractures.

B. Procedure For Anterior Cruciate Ligament Reconstruction

In one embodiment, the invention may be utilized for the insertion of a bone-patellar tendon-bone autograft in anterior cruciate ligament reconstruction surgery. During anterior cruciate ligament reconstruction, the pin passer and pin may be passed through previously drilled tibial and femoral tunnels, and then the pin passer may be used to pull a suture through the tunnels, which in turn is used to pull the anterior cruciate ligament graft into place within the knee. The pin may be left in place within the knee to be used as a guide for headless cannulated screws used to secure the graft in place. The problems of procurement of grafts, potential rejection, and AIDS are avoided. The procedure may be routinely done as an outpatient surgery. The incisions may be small and cosmetically pleasing and the procedure is usually completed with tourniquet times under one hour. The procedure allows diagnostic arthroscopy and the surgeon is not committed to the anterior cruciate ligament reconstruction unless it is confirmed by the arthroscopic findings. The skilled arthroscopist should obtain reliable results without requiring the use of an image intensifier. The procedure allows for accurate isometric anatomic positioning without the need for isometry or the use of a tensiometer. The procedure provides excellent immediate reproducible fixation and early aggressive range of motion and weight bearing without loss of fixation.

Figure 15:
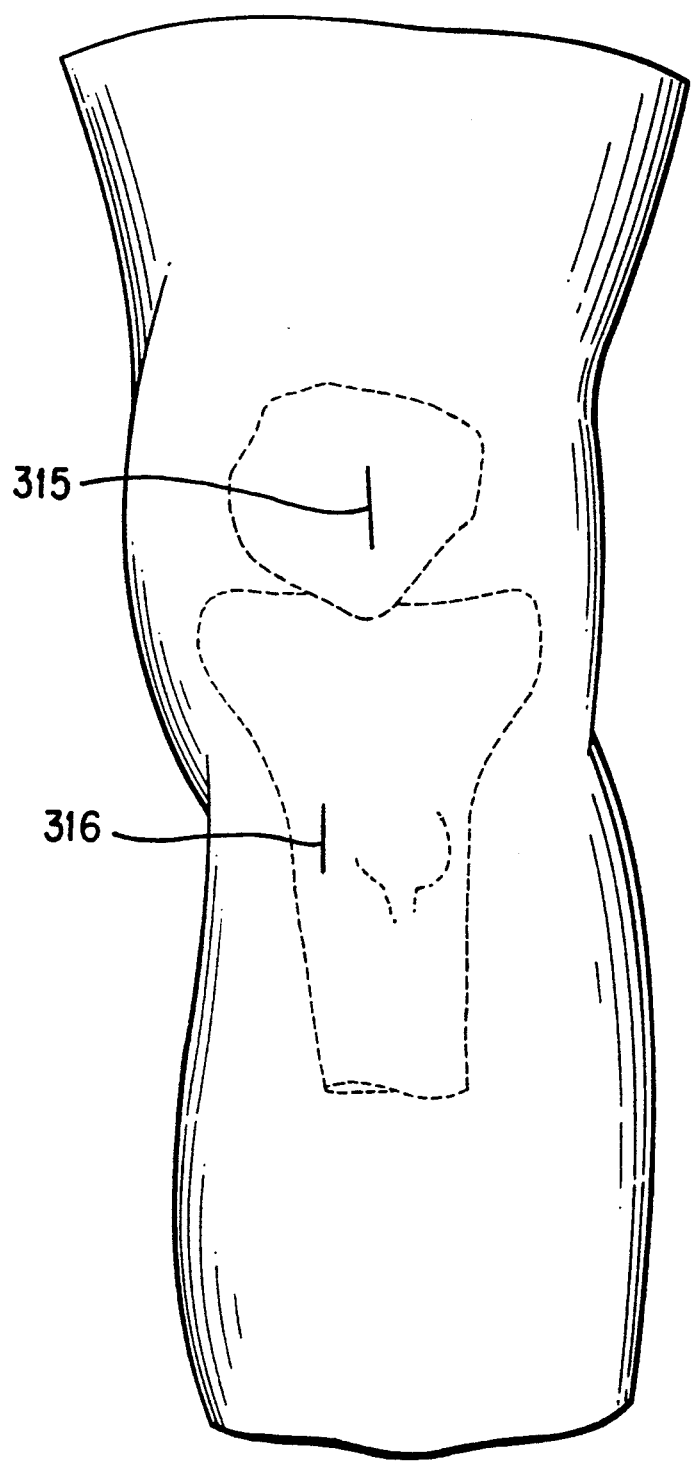

Vertical incisions may be made on the patella and medial to the tibial tubercle that are approximately 2.5 cm in length (FIG. 15). The skin incisions may be undermined in such a fashion as to provide sufficient mobility for retraction, while harvesting the patellar and tibial bone plugs. A carefully placed anteromedial incision 316 may begin approximately 1 cm medial to the tibial tubercle and 2 cm distal to the joint line, extending for 2.5 cm. The patellar incision 315 may begin at the distal pole of the patella and extend proximally over the midline of the patella for 2.5 cm. The tibial incision may be also used for placement of the tibial tunnel and subsequent fixation of the graft. (Previously, the direction of the incisions were transverse and parallel to Langer's lines. This resulted in an 8% reoperative rate for the removal of intra-articular adhesions and arthrofibrosis and one case of intrapatellar contracture syndrome.) The procedure may be now done using vertical incisions (Mark Purnell, M.D., Aspen, Colo., personal communication) and has resulted in only a 4% reoperative rate. With vertical incisions there have been no cases of intrapatellar contracture syndrome. Using this procedure, the morbidity ascribed to using a patellar tendon graft that has been reported by others has not been encountered.

Figure 16:
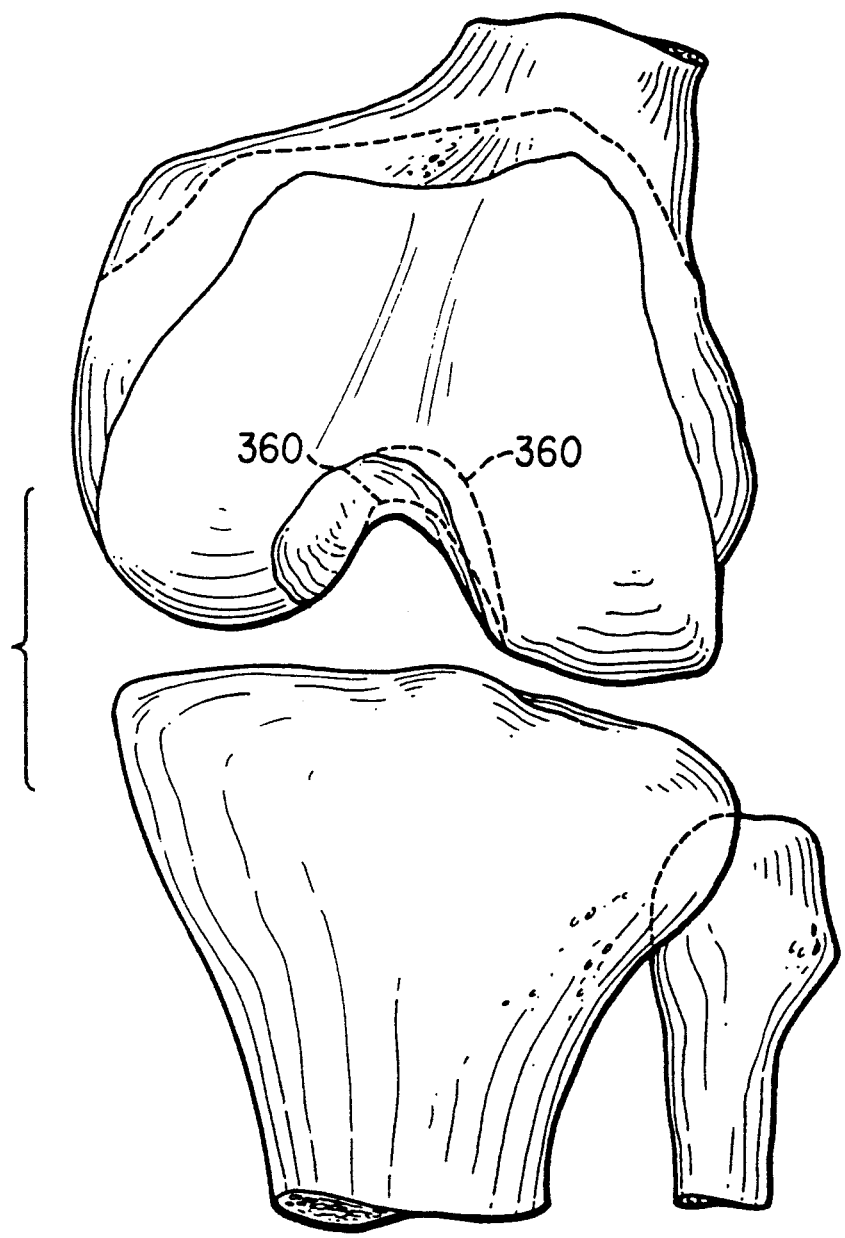

Arthroscopic diagnostic completion of all other procedures such as meniscectomy, meniscal repair, removal of loose bodies, debridement of anterior cruciate ligament tear, etc., may be accomplished without tourniquet control in order to allow sufficient time for the ACL reconstruction procedure. Notchplasty may be commenced under tourniquet control. The boundary of the notchplasty is shown as contour 360 in FIG. 16, and should be sufficiently wide (approximately 2 cm) and must be sufficiently posterior to include the posterior lateral femoral cortex in order to ensure accurate placement and subsequent isometricity.

Figure 17:
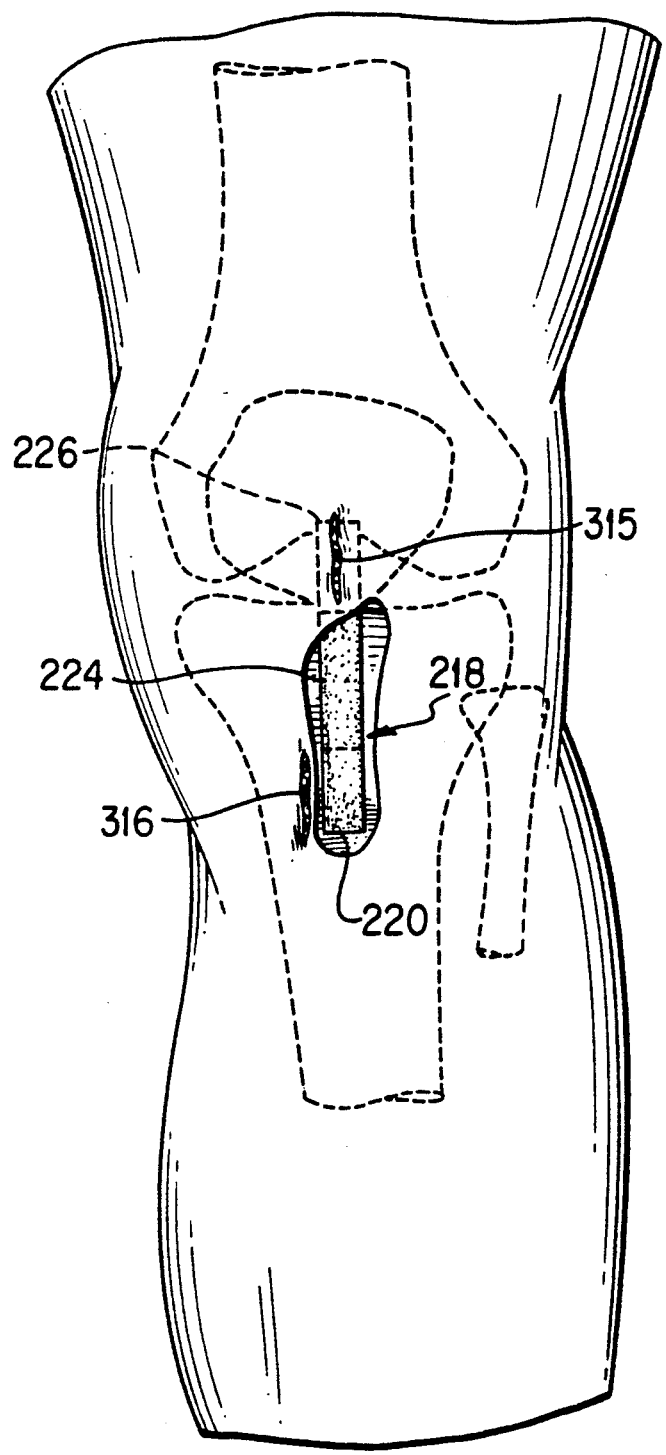

A patellar tendon harvest 218 (FIGS. 17 and 18) may be taken through the vertical incisions 315 and 316, and may be harvested with an oscillating saw. The tibial tubercle portion 220 may be harvested first with a width of 10 mm. The central one third portion 224 of the patellar tendon may be harvested using a Smillie meniscotome. The patellar portion 226 may be harvested with a width of approximately 11 mm, with care taken to avoid the proximal portion of the patella and potential interruption of the quadriceps tendon insertion. The precise width and length can be varied according to the size of the patient. The resultant "V" shaped patellar defect may be contoured with a high speed burr and filled with bone chips removed in preparation of the graft.

Figure 20:
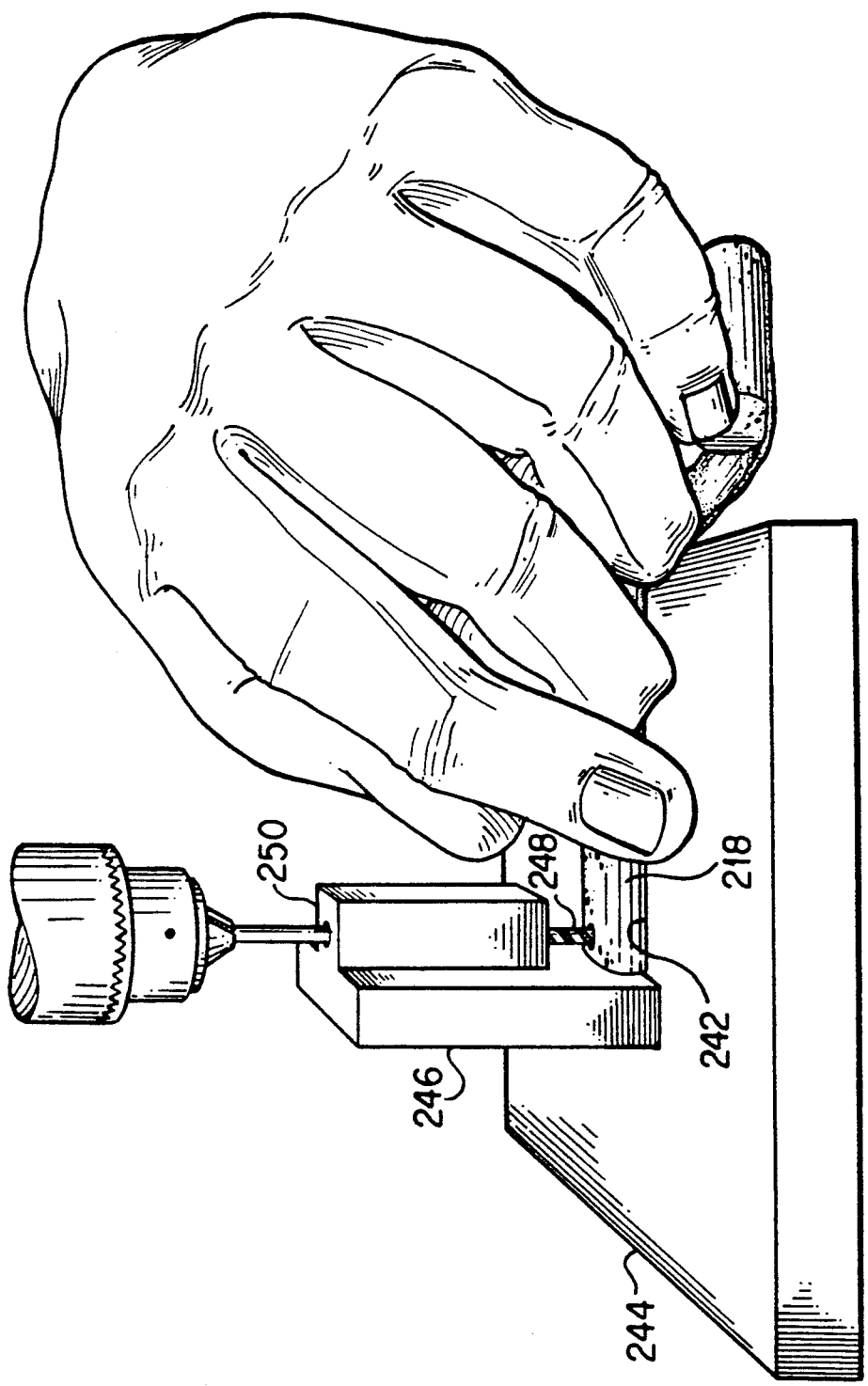
Figure 26:
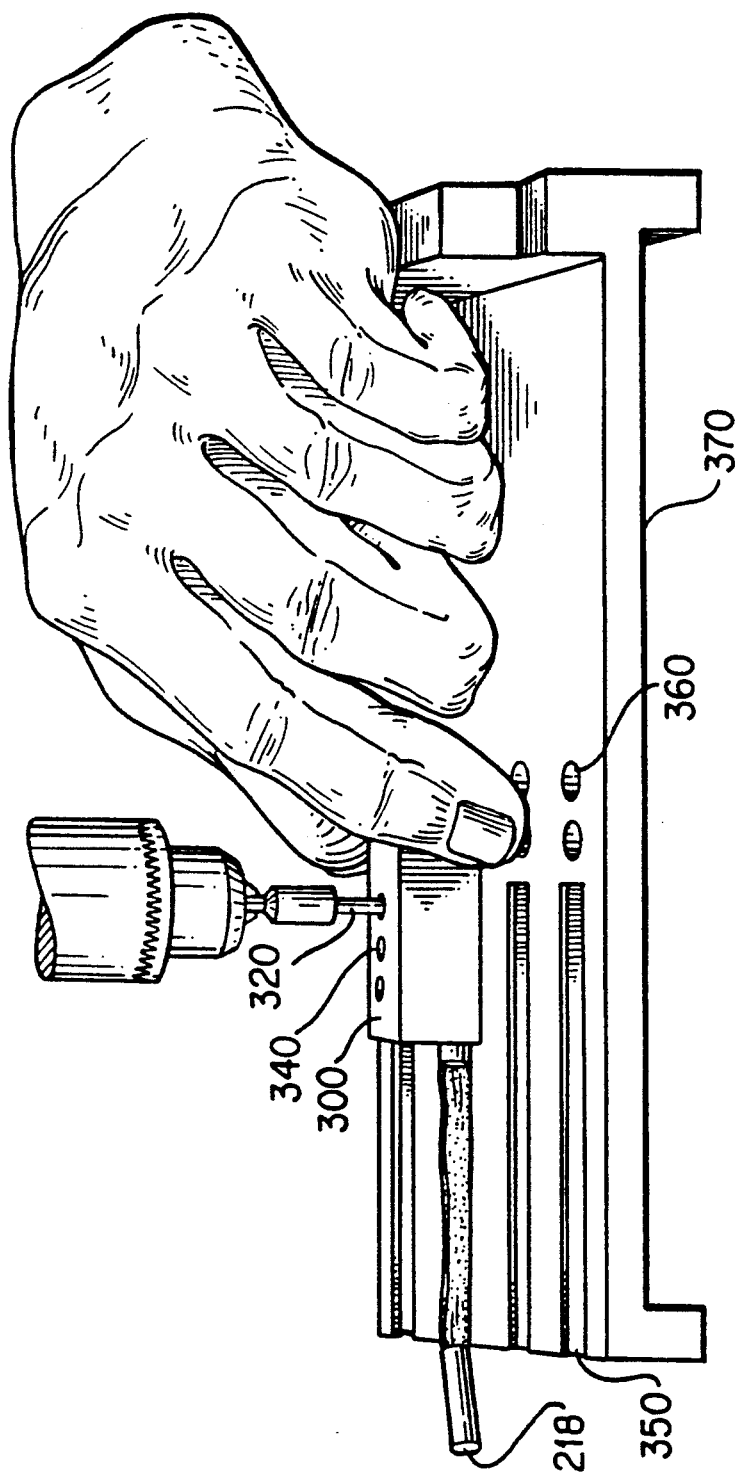
FIG. 26 depicts an alternative embodiment of the drill guide of FIG. 20, which may be used for drilling a hole in the bone-tendon bone autograft.

The graft may be prepared at a side table by removing the acutely angled portion of the bone plug to approximate a trapezoidal shape. The graft 218 may be passed through an appropriate sizing cylinder 230 to ensure easy passage through an appropriately sized bone tunnel (FIG. 19). A single drill hole may be placed in the bone plugs of the graft using drill guide 240 (FIG. 20). The drill guide 240 includes base 244 and guide tower 246. The guide tower includes drill bit guide hole 250 for insertion of drill bit 248. Base 244 includes trough 242 into which the bone plugs of the graft may be placed when drilling holes in the bone plugs. A zero Ethibond (Ethicon Division of Johnson and Johnson, Somerville, N.J. 08876) suture may be placed in the smaller bone plug and a 24 gauge flexible wire may be placed in the larger bone plug. An alternative embodiment of a drill guide is shown in FIG. 26. In this embodiment, the drill guide may include a guide tower 300, which may be removable inserted into the base 370 by means of the receiving slots 360 located on the base. The bone-tendon-bone autograft 218 may be removably inserted into one of the various sized guide slots 350 during the drilling of the bone plugs. A plurality of drill bit guide holes 340 in the guide tower 300 allow the user to drill the required number of holes in the required location on the bone plug.

Figure 21:
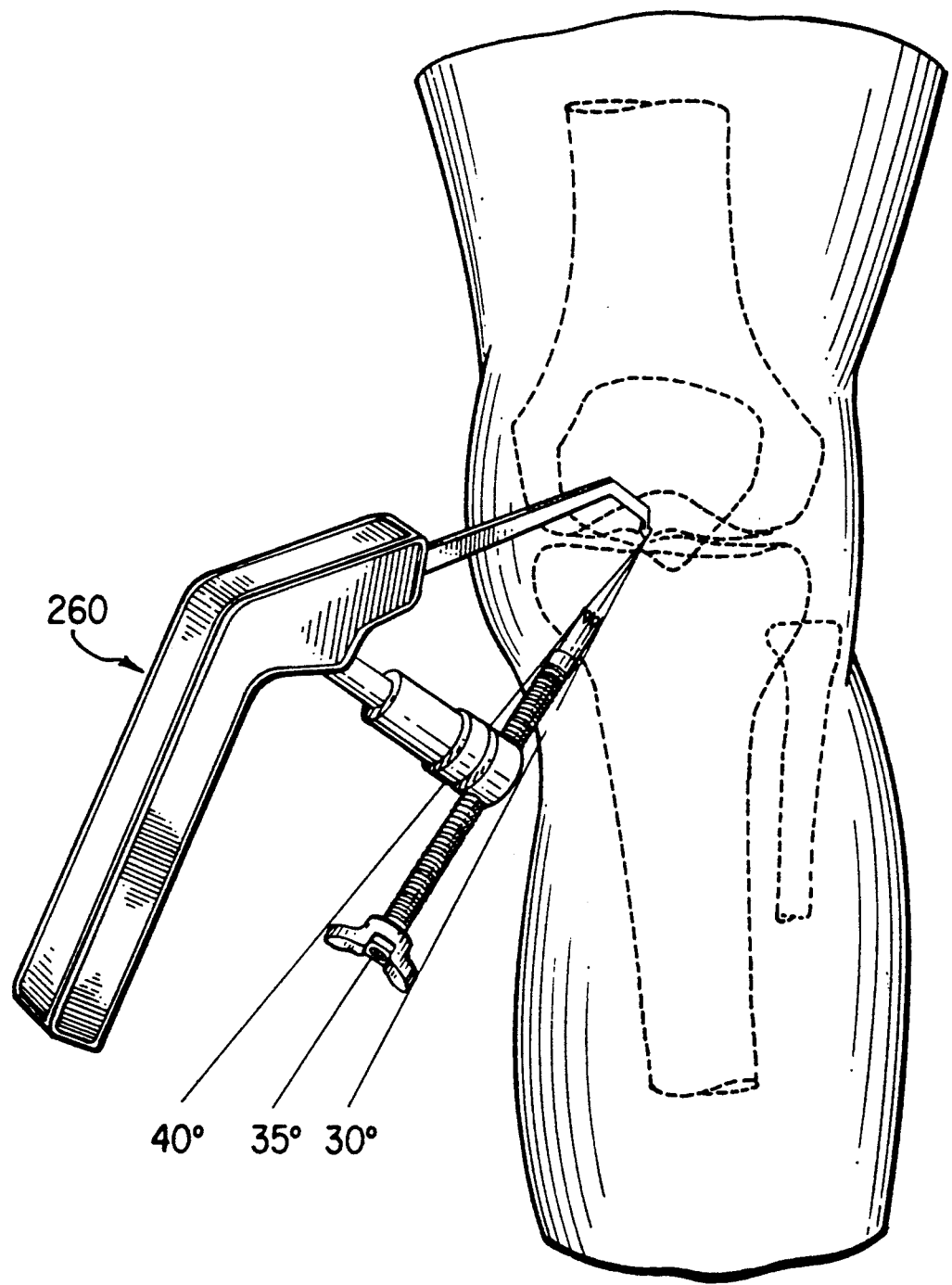

The tibial and femoral portals may be predrilled to match the size of the outside diameter of the graft ends which are bone. A Concept ™ Tibial Drill Guide 260 (Linvatec Corporation, 11311 Concept Boulevard, Largo, Fla. 36643) may be used to place a pilot pin at the anatomic center of the anterior cruciate ligament at an angle of approximately 35 degrees (FIG. 21). A trochar may be placed on top of the knee along the same line to see the approximate angle and exit point of the beath pin laterally so that it is not too far proximal on the thigh. The pilot pin is inserted through the same incision that is used to harvest the tibial portion of the graft. An 11 mm cannulated reamer may be used to create the tibial tunnel. If the tibial tunnel is too far posterior it will not be isometric except by bone grafting or some other measure. If the tibial tunnel is too far anterior, the posterior wall can be beveled to attain more isometric placement. If the tibial tunnel is too far medial, the graft will impinge on the medial femoral condyle and the articular surface of the tibia. If the tibial tunnel is too far lateral the graft will impinge on the lateral femoral condyle and the notchplasty.

Figure 22:
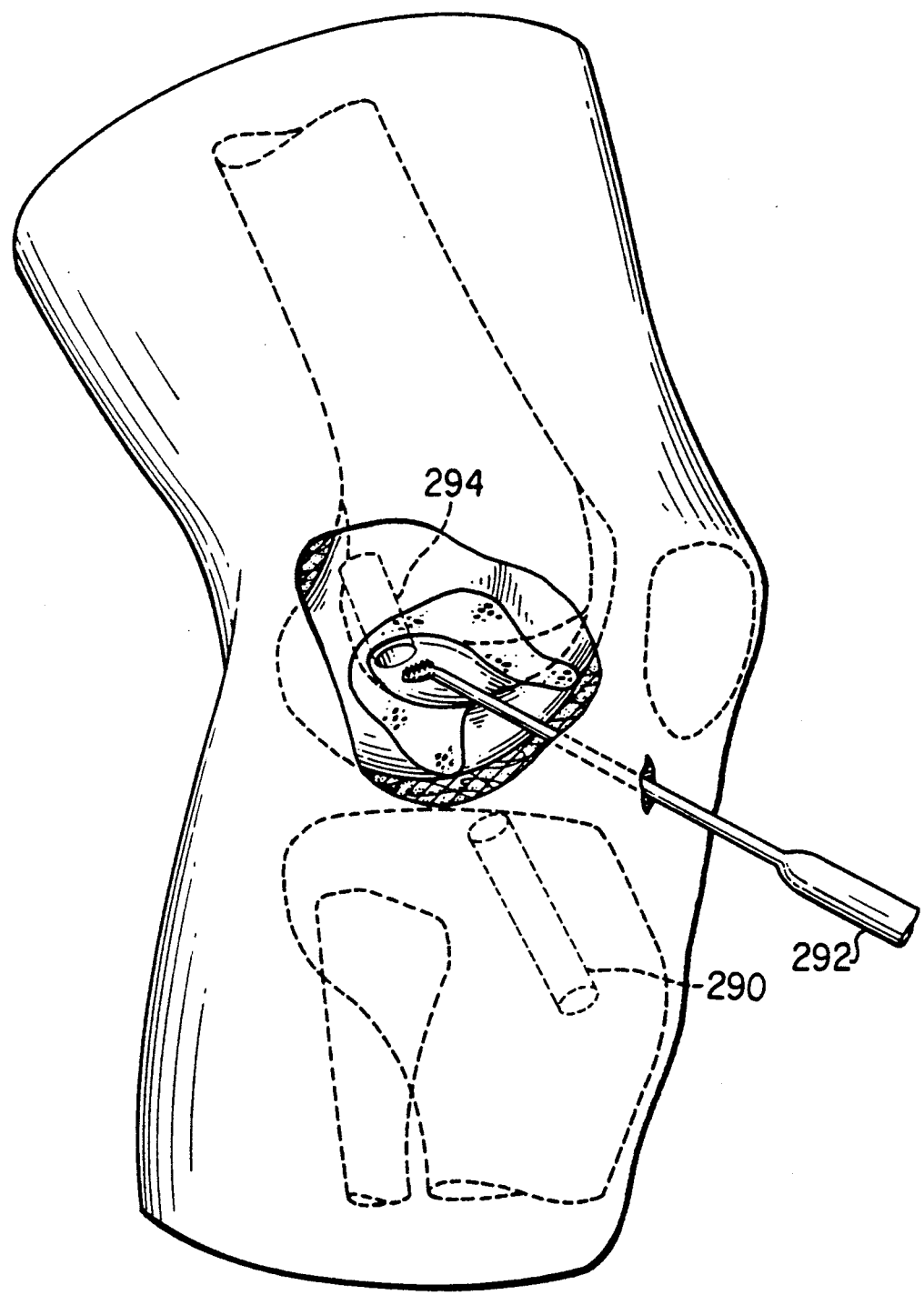

The femoral tunnel should be placed high in the notch at approximately 6-7 mm anterior to the posterior cortex. The pilot pin may be advanced and exits through the lateral femoral cortex but not through soft tissue. A 10 mm cannulated reamer may then be advanced over the pilot pin through the tibial tunnel and the footprint of the reamer may be created and examined to ensure accurate positioning of the femoral tunnel. The width of the posterior cortex remaining should be approximately 1-2 mm. If the posterior margin is more than 2 mm thick, the pilot pin should be reinserted posteriorly, and the footprint checked before reaming the entire tunnel. After adequate positioning is determined, the 10 mm reamer may be advanced through the lateral femoral cortex. It is also necessary to be sure that the tunnel is not too far posterior, thereby creating a trough instead of a tunnel. The margins of both the tibial and femoral tunnels may be chamfered to avoid damage to the graft (FIG. 22).

Figure 23:
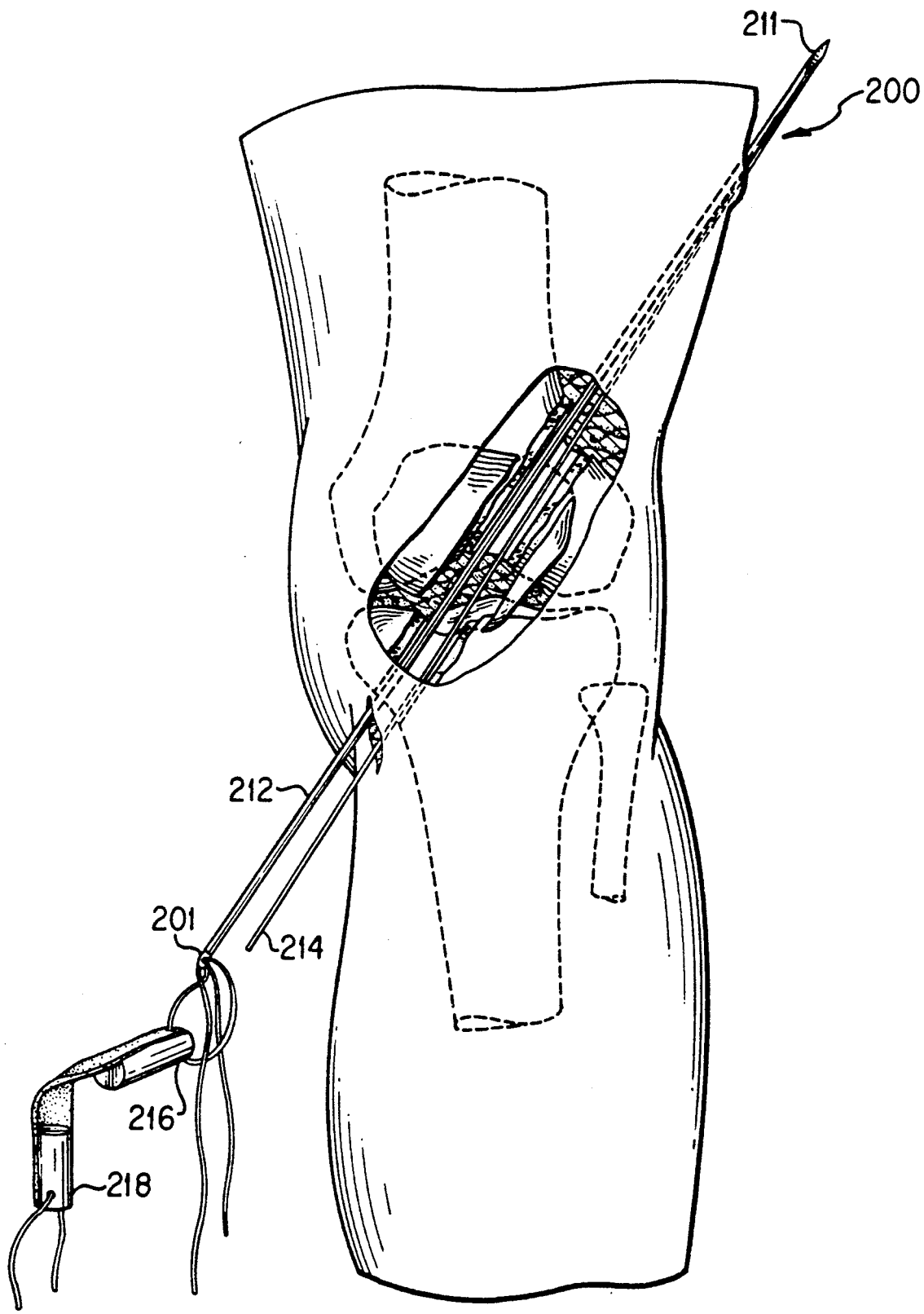

After the creation of the tibial and femoral bone tunnels, the system 200, including passer 212 and guide pin 214, which may be comprised of a flexible metal composite such as Nitinol ™, may be passed through the tunnels, exiting through a puncture wound (FIG. 23). A hollow tube may be used to assist in passing the system through the two predrilled portals. The system may be inserted through the same incision that is used to harvest the tibial portion of the graft. A suture 216, attached to the bone autograft 218, may be threaded through eye 200 on the pin passer 212. After the system 200 is through the puncture wound, the guide pin 214 may be backed out of the pin passer 212. The pin passer may then be pulled through the tunnels and used to manipulate the graft into place, while leaving the pin in place, anterolateral to the graft.

A grasper may be used to hold the femoral portion of the graft in place and the Ethibond suture may be removed. A headless cannulated screw may then be advanced down pin 214 through the lateral puncture wound until the tip of the screw is barely visible within the knee, to fix the femoral portion of the graft. In the femoral tunnel, the pin must be as far superior in the notch as feasible while still allowing for adequate clearance for the screw and the screwdriver coming from outside-in, proximal lateral so as to clear a leg holder used to hold the leg during surgery. The leg holder and the tourniquet must be placed as high on the thigh as possible so as to allow for sufficient room for the screwdriver. The leg holder cannot have a lot of bulk over the lateral aspect as the screwdriver is rigid and needs to follow the guide pin 214 down.

An alternate method of screw replacement would involve an "inside-out" technique. This would utilize an angled, gear-driven screwdriver, which would neutralize the difficulties involved with the outside-in technique and the leg holder. A grasper through the anteromedial portal is used to guide the nitinol wire from inside the compartment out of the anteromedial portal. One end of the screw is then attached upon the end of the angled screwdriver and the other end of the screw is applied to the nitinol wire. The screw is then guided through the anteromedial portal to the entrance of the femoral tunnel by simultaneously turning and pushing the screwdriver while pulling the nitinol wire. The screw is then advanced until adequate fixation is obtained.

If the pin does exit too far proximally lateral, it may be necessary to remove the leg from the leg holder in order to get the screw in. Under no circumstances should the screw be advanced unless the screwdriver is parallel to the pin. If it is advanced and is not parallel, the pin will kink and the screw will not enter the tunnel but will bite into the pin and not advance. A lateral incision would then need to be made to retrieve the screw.

If the femoral tunnel is too far posterior and fixation cannot be attained and the graft pulls out, a trough has probably been created posteriorly. Rather than attempt multiple passes with an interference fit screw, a cerclage can be formed from an 18 gauge wire and attached to the femoral portion of the graft. A lateral incision may then be made and the wire may be fixed with an ASIF or similar screw placed through the femur.

Figure 24:
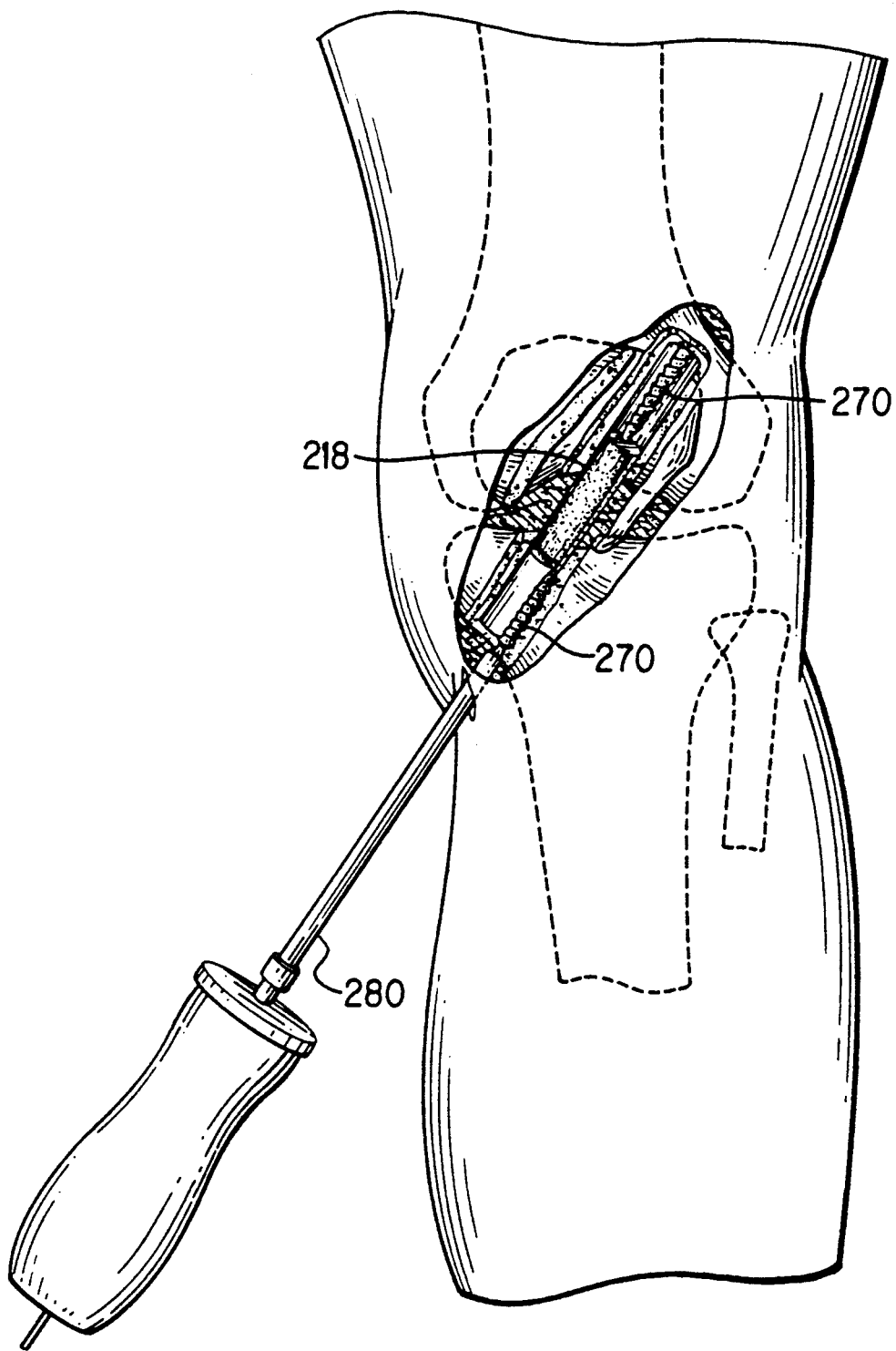
Figure 25:
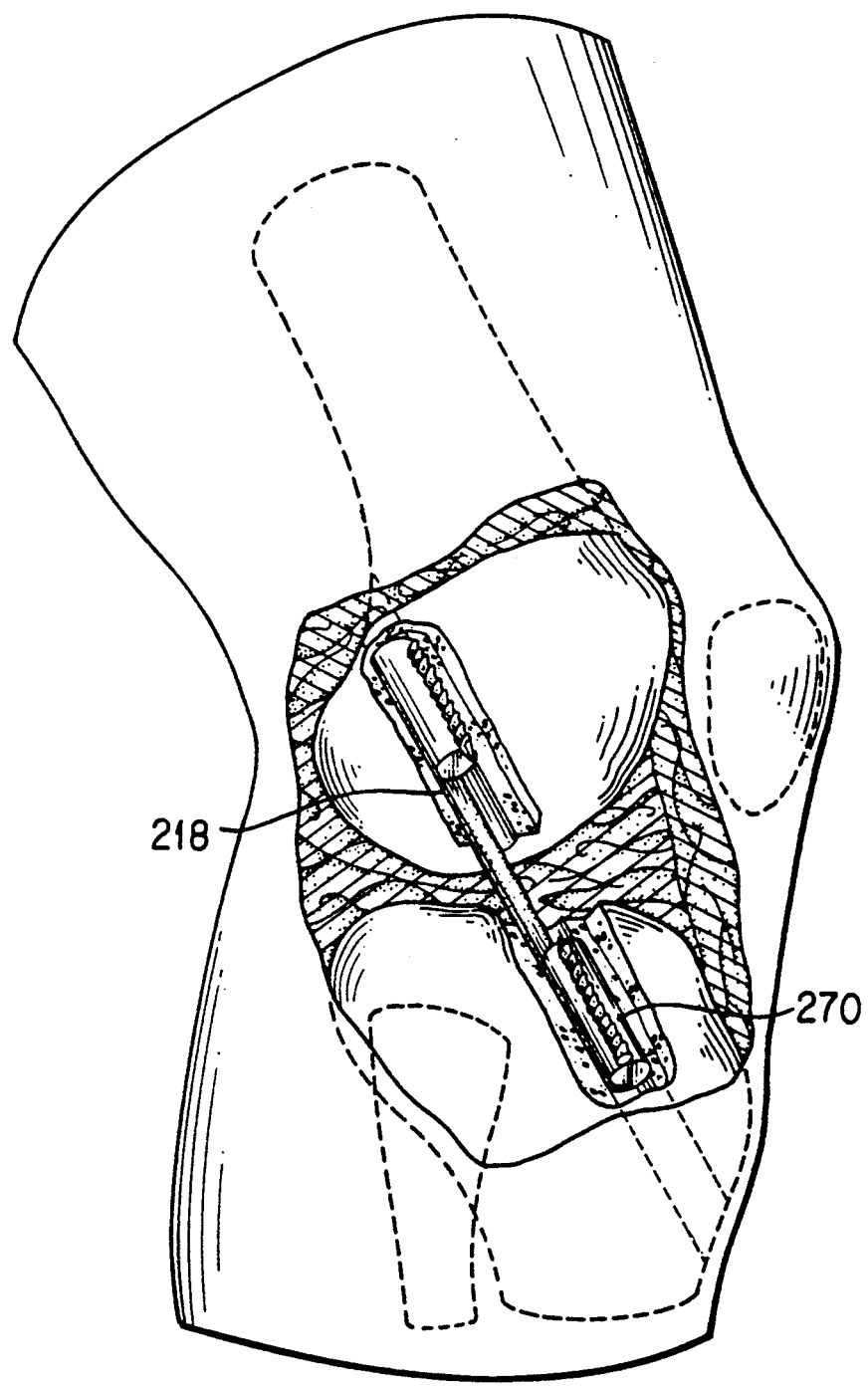

Following insertion of the femoral screw, the guide pin may be retracted but not removed to allow cycling of the knee, to ensure the absence of impingement, and verify isometricity. The knee should not be bent when the guide pin is through the tibial and femoral tunnels, as this will kink the pin causing difficulty in removing it following femoral fixation. A kocher clamp may be used to apply adequate tension on the tibial portion of the graft, while a headless cannulated screw 270 may be placed over the remaining portion of the guide pin 214 to fix the tibial portion, using a cannulated screw driver 280 (FIG. 24). The guide pin is then removed. Any portion of the graft protruding from the tibial tunnel may be rongeured smooth.

Closure may be effected with a subcuticular absorbable suture. A sterile dressing and a hinged knee immobilizer may be applied. For pain control, a Patient Controlled Anesthesia (PCA) pump and Buccal Morphine may be used. Bell et al. (1985) Lancet, January 12, p. 71-73. To avoid reoperation and loss of motion an aggressive range of motion program must be followed.

The femoral tunnel in an alternative embodiment of the invention may be drilled as a blind tunnel, to advantageously preserve more of the bone of the patient. In this embodiment, after insertion of the system 200 into the previously drilled tibial tunnel and the blind femoral tunnel, the trocar point 211 on the pin passer 212 may allow the system to be driven through the bone at the blind end of the femoral tunnel by means of a mallet.

The invention may be utilized in a wide range of surgical procedures, to assist in placing an object such as a graft in a biological tissue. The outside diameter variations of the system could be configured to coincide with potential fixation device diameters. Overall lengths could also be adjusted in order to reduce the potential bending of the passer. For example, if there is a fractured femur combined with osteoporosis, a fixation device, other than a typical screw, which would be cannulated, could be assembled from both sides of the femur arthroscopically using the pin as the cannula and alignment tool, helping to position the bone fragments during the fixation process.

What is claimed is:

1. A system for the insertion of an object into biological tissue comprising:
   (i) a pin; and
   (ii) a pin passer having an elongate body and first and second ends and the passer including:
      (a) pin receiving means for removably receiving the pin, the pin receiving means including a blind channel in the body, proximal to the first end, with an entrance notch for removably receiving the pin; and
      (b) object attachment means, located at the second end, for removably attaching the object;
   the passer having cross sectional dimensions substantially smaller than 2.5 cm, so as to permit its passage through a portal in the course of surgery to repair a bone or joint.

2. A system according to claim 1, wherein the passer includes a slot for receiving the pin, the slot extending from the notch proximally to the second end; and
   wherein the slot is suitably configured to securely engage the pin, such that the pin may be removably inserted past the notch into the blind channel and secured into place in the slot.

3. A system according to claim 2, wherein the passer includes a trocar point at the first end.

4. A system according to claim 3, wherein the slot further extends from the notch towards the first end of the passer.

5. A system according to claim 3, wherein the pin is a flexible metal wire, capable of bending and returning to its original shape.

6. A system according to claim 5, wherein the pin is made of an alloy of nickel and titanium.

7. A system according to claim 6, wherein the pin has a diameter of approximately 0.064 inches, and the length of the wire is approximately 9 to 14 inches.

8. A system according to claim 7, wherein the notch in the pin passer is disposed at angle of approximately 3° to 8° with respect to the passer.

9. A system according to claim 2, wherein the attachment means on the pin passer is an eye.

10. A system according to claim 2, wherein the first end of the pin passer includes a twist drill tip to provide a pin passer system that may be removable attached to a drill chuck and inserted into the tissue by drilling.

11. A method for the insertion of an object into biological tissue comprising:
  (a) obtaining a system comprised of a pin and a pin passer, the pin passer having an elongate body with first and second ends and including:
    (i) a blind channel in the body, proximal to the first end, with an entrance notch for removably receiving the pin;
    (ii) object attachment means for removable attachment of the object, located at the second end;
    (ii) a slot for receiving the pin, the slot extending from the notch proximally to the second end, such that the pin may be removably inserted past the notch into the blind channel and secured into place in the slot;
  (b) inserting the first end of the pin passer, and pin inserted therein, into a proximal side of the tissue, through the tissue and then out of a distal side of the tissue, such that the first end of the pin passer and the pin protrude out of the distal side of the tissue and the second end of the passer and the pin protrude from the proximal side of the tissue;
  (c) attaching the object to the attachment means on the pin passer;
  (d) disengaging the pin and the passer;
  (e) pulling the first end of the passer and the object attached thereto until the passer is pulled out of the tissue on the distal side and the object is pulled to a desired position in the tissue, while leaving the pin in place, such that the pin protrudes from the proximal and distal sides; and
  (f) disengaging the passer from the object.

12. A method according to claim 11, further comprising:
  (g) using the pin to guide the insertion of an engagement means for engaging the object with the tissue at the proximal and distal sides of the tissue; and
  (h) removing the pin.

13. A method according to claim 12, wherein, in step (a), the passer includes a trocar point at the first end; and
  wherein, in step (b) the trocar point is used to create a channel in the tissue as the system is inserted through the tissue.

14. A method according to claim 12, wherein the tissue is bone, and wherein, in step (a), the first end of the passer includes a twist drill tip; and
  wherein in step (b), the system is attached to a drill chuck, drilled through the bone and then the drill chuck is removed.

15. A method according to claim 12, for anterior cruciate ligament reconstruction, wherein the tissue is the knee and the object is a femoral bone insert-patellar tendon-tibial bone insert autograft;
  wherein step (b) further comprises inserting the first end of the passer, and pin inserted therein, into a proximal side of the knee and through the femur and then the tibia, and then out of a distal side of the knee, such that the first end of the passer and the pin protrude out of the distal side of the knee and the second end of the passer and the pin protrude from the proximal side of the knee;
  wherein step (e) further comprises pulling the first end of the passer and the graft attached thereto through the knee until the passer is pulled out of the knee on the distal side, and pulling the graft to a desired position in the knee such that the femoral and tibial inserts are placed in a desired position within the femur and tibia respectively;
  wherein step (g) further comprises:
    (i) placing a headless cannulated screw over the pin on the distal side of the knee and guiding the insertion of the screw into the femur to fix the femoral portion of the bone graft;
    (ii) pulling the pin from the proximal side of the knee until the pin is removed from the femur and remains in the tibia, and flexing the knee to ensure the absence of impingement and to verify isometricity; and
    (iii) placing a headless cannulated screw over the pin on the proximal side of the knee and guiding the insertion of the screw into the tibia to fix the tibial portion of the bone graft; and
  wherein step (h) further comprises removing the pin by pulling the pin out from the proximal side of the knee.

16. A method according to claim 15, wherein the knee into which the system is inserted, in step (b), includes predrilled femoral and tibial bone tunnels; and
  wherein the diameter of the femoral and tibial bone tunnels is approximately equal to the diameter of the tibial and femoral inserts of the autograft respectively.

17. A method according to claim 16, wherein the pin is a flexible steel wire, capable of bending and returning to its original shape.

18. A system according to claim 17, wherein the pin is made of an alloy of nickel and titanium.

19. A method according to claim 18, wherein the pin has a diameter of approximately 0.064 inches, and a length of approximately 9 to 14 inches.

20. A method according to claim 19, wherein notch in the pin passer is disposed at an angle of approximately 3° to 8° with respect to the passer.

21. A method according to claim 17, wherein the attachment means is an eye.

22. A method according to claim 16, wherein the predrilled femoral tunnel is a blind tunnel.

* * * * *